(12) United States Patent
Rey et al.

(10) Patent No.: US 11,365,169 B2
(45) Date of Patent: Jun. 21, 2022

(54) METHOD FOR SYNTHESISING VITAMIN A

(71) Applicant: ADISSEO FRANCE S.A.S., Antony (FR)

(72) Inventors: Patrick Rey, Lyons (FR); Robert Huet, Paris (FR); Jean-Michel Joerger, Villeurbanne (FR); Vivien Henryon, Lyons (FR)

(*) Notice: Subject to any disclaimer, the term of this patent is extended or adjusted under 35 U.S.C. 154(b) by 0 days.

(21) Appl. No.: 17/269,096

(22) PCT Filed: Aug. 19, 2019

(86) PCT No.: PCT/EP2019/072084
§ 371 (c)(1),
(2) Date: Feb. 17, 2021

(87) PCT Pub. No.: WO2020/038858
PCT Pub. Date: Feb. 27, 2020

(65) Prior Publication Data
US 2021/0309597 A1 Oct. 7, 2021

(30) Foreign Application Priority Data
Aug. 20, 2018 (FR) ...................... 1857549

(51) Int. Cl.
C07C 45/65 (2006.01)
C07C 29/17 (2006.01)
C07C 315/00 (2006.01)
C07C 47/225 (2006.01)
C07C 315/02 (2006.01)

(52) U.S. Cl.
CPC .............. *C07C 45/65* (2013.01); *C07C 29/17* (2013.01); *C07C 47/225* (2013.01); *C07C 315/02* (2013.01); *C07C 2601/16* (2017.05)

(58) Field of Classification Search
CPC ........ C07C 45/65; C07C 29/17; C07C 315/02
See application file for complete search history.

(56) References Cited

FOREIGN PATENT DOCUMENTS

| EP | 1031561 A1 | 8/2000 |
| FR | 2359822 A1 | 2/1978 |
| WO | 2012175398 A1 | 12/2012 |

OTHER PUBLICATIONS

International Search Report dated Nov. 22, 2019 re: Application No. PCT/EP2019/072084, pp. 1-2, citing: FR 2359822 A1, EP 1031561 A1 and WO 2012175398 A1.

*Primary Examiner* — Sikarl A Witherspoon
(74) *Attorney, Agent, or Firm* — Cantor Colburn LLP

(57) ABSTRACT

A method for preparing a compound of formula (I)

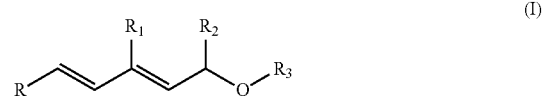

in which
R1 is selected from H and alkyls,
R2 is selected from H, alkyls, OR' where R' is selected from alkyls, silyls, CO-alkyl,
R3 is selected from the acyl groups of the CO(R") type, and the CO(OR"), CO(NR"R'"), PO(OR")(OR'"), PO(OR")(R'") groups where R" and R'", independently of each other, are selected from H and alkyls,
R represents a C(R4)=C(R5)(R6) group where R4, R5 and R6, independently of each other, are selected from H, linear or cyclic alkyls and alkenyls, aryls, alkylaryls, or R4 and R5 together form a saturated or unsaturated, substituted or unsubstituted ring,
from a compound of formula (II)

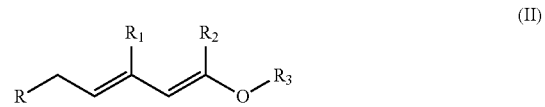

or a compound of formula (III)

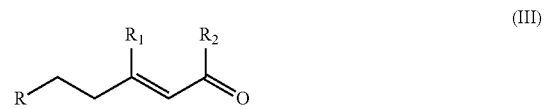

in which, R, R1, R2 and R3 have the above definition.

12 Claims, No Drawings

METHOD FOR SYNTHESISING VITAMIN A

The present disclosure relates to new sesquiterpene compound conversion reactions allowing opening a new pathway of access to vitamin A ($C_{20}H_{30}O$), the precursors thereof and the derivatives thereof.

The industrial-scale synthesis of vitamin A is carried out by various conventional methods. Among other preparations, vitamin A can be obtained by the so-called C15+C5 condensation pathway, for example the so-called *Julia* reaction which involves the chemistry of sulfones, according to which the vinyl-β-ionol is treated with a phenylsulfinate anion for leading to a C15 sulfone to which an allyl bromide is added to obtain a C20 sulfone. This is then converted, by elimination, into vitamin A acetate which is generally used as is, the vitamin A being very unstable, or saponified into vitamin A.

Other methods are also used. Thus, the vitamin A can be made by a C15+C5 coupling method via a Wittig reaction; this method nonetheless implements intermediates with carcinogenic, mutagenic or toxic effects for the reproduction (CMR), such as C5 acetate, and requires a unit for regenerating phosphine with phosgene, which is a very toxic gas.

Thus, according to the document FR2359822A1, a method for synthesizing vitamin A acetate from vinyl-β-ionol is known, consisting in reacting a β-ionylidene-ethyl-triphenylphosphonium salt in aqueous solution with γ-acetoxy-glitic aldehyde.

Another pathway of access lies in a C6+C14 coupling method through alkyne chemistry; it has the drawbacks of using some raw materials, such as acetylene and nButyl-Li, which present obvious HSE (Health-Safety-Environment) risks and of involving epoxy intermediates which are not very stable and toxic.

These synthesis methods have not undergone any real evolutions since their discovery, and to date, it is important to use new industrial synthesis methods which are safer and more economical.

The disclosure provides an original pathway for the synthesis of the C15 sulfone, from sesquiterpenes, and in particular farnesene, or sesquiterpene derivatives, opening a new paradigm in the synthesis of vitamin A. The compounds at the start of this new pathway are present in nature, they are found in some plant essences from which they can be extracted, they are also biosynthesized by microorganisms, in particular fungi. The reagent resource being therefore inexhaustible, the disclosure provides a sustainable solution to the cost problems of the conventional methods and contributes to a real progress in the manufacture of vitamin A, but also that of intermediates for other syntheses.

The disclosure provides a method for preparing a compound of formula (I)

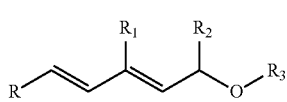

(I)

in which
R1 is selected from H and alkyls,
R2 is selected from H, alkyls, OR' where R' is selected from alkyls, silyls, CO-alkyl,
R3 is selected from the acyl groups of the CO(R") type, and the CO(OR"), CO(NR"R'"), PO(OR")(OR'"), PO(OR") (R'") groups where R" and R'", independently of each other, are selected from H and alkyls, by way of example R3 is $CO(CH_3)$ or $CO(CH_2CH_3)$, R represents a C(R4)=C(R5)(R6) group where R4, R5 and R6, independently of each other, are selected from H, linear or cyclic alkyls and alkenyls, aryls, alkylaryls, or R4 and R5 together form a saturated or unsaturated, substituted or unsubstituted ring, by way of example, R represents:
the structural portion of the carbon atom in 1 to the carbon atom in 10 of a retinoid, illustrated below

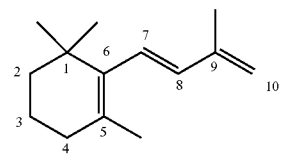

or the structural portion of the carbon atom in 1 to the carbon atom in 10 of a 7,8-dihydro-retinoid, illustrated below:

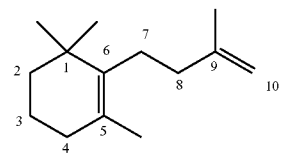

or the structural portion of the carbon atom in 1 to the carbon atom in 6 of a retinoid, illustrated below

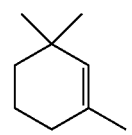

said compound of formula (I) being obtained by reacting a compound of formula (II)

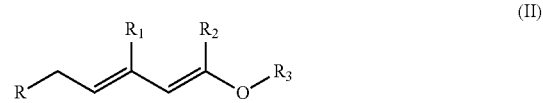

(II)

in which, R, R1, R2 and R3 have the above definition,
in the presence of a strong base or in the presence of a metal catalyst.

Another of the advantages of the disclosure, which constitutes a pivot of the disclosure, is a one-pot method for obtaining a compound (I) above, from a compound of formula (III)

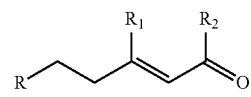

(III)

in which

R, R1 and R2 have the above definition.

said method comprising the formation of the compound of formula (II)

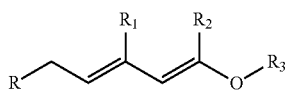
(II)

in which, R, R1, R2 and R3 have the above definition, from said compound (III) above, and the formation of compound (I), according to the isomerization method described above, from compound (II). Advantageously, the compound (II) is not isolated. This one-pot isomerization/acylation method represents a real progress in the synthesis of vitamin A, the precursors thereof and the derivatives thereof.

Before discussing the disclosure in more detail, the definitions of terms used in the present text are given below.

Any reference to an unsaturated compound extends to the isomers of this compound, in particular to the regioisomers and stereoisomers thereof.

By way of example, the term farnesene includes the alpha and beta regioisomers of farnesene, as well as the stereoisomers of each of them, as illustrated below:

α-farnesene (3,7,11-trimethyl-1,3,6,10-dodecatetraene) having the following formula

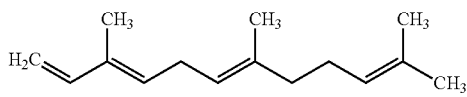

which can exist in the form of the following 4 isomers (3E, 6E), (3E, 6Z), (3Z, 6Z) and (3Z, 6E), and β-farnesene (7,11-dimethyl-3-methylene-1,6,10-dodecatriene) having the following formula

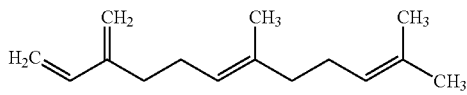

which can exist in the form of the following 2 isomers (6E) and (6Z).

This definition applies in particular to farnesal, dehydrofarnesal, farnesol, retinal, dihydroretinal, the acetates thereof and the enol acetates thereof, whose names cover all respective isomers thereof.

According to the disclosure, an alkyl group means a saturated, monovalent, linear, cyclic and/or branched hydrocarbon chain including 1 to 20 carbon atoms, preferably 1 to 6 carbon atoms, representative elements of which are for example the following: the methyl, ethyl, n-propyl, iso-propyl, n-butyl, sec-butyl, iso-butyl, tert-butyl, pentyl, hexyl groups. An alkyl group with a cyclic hydrocarbon chain, means a saturated, monovalent hydrocarbon chain including 3 to 20 carbon atoms, preferably 3 to 7 carbon atoms, and one or several ring(s). Representative elements are for example the following: the cyclopropyl, cyclobutyl, cyclopentyl, cyclohexyl, cycloheptyl, norbornyl groups.

An alkenyl group means a monovalent, linear, cyclic and/or branched, mono- or poly-unsaturated hydrocarbon chain comprising 2 to 20 carbon atoms.

A silyl group means a group consisting of an Si atom substituted by 3 identical or different substituents selected from H and alkyls, such as trimethylsilyl.

An aryl group according to the disclosure means an aromatic, monofunctional, monocyclic or polycyclic hydrocarbon chain, comprising 6 to 20 carbon atoms. By way of example, benzyl, naphthyl and biphenyl groups may be mentioned.

The terms «alkyl» and «aryl» as defined above maintain the same definition when they include the name of a group, for example in the —CO-alkyl or alkylaryl groups.

According to a variant of any one of the above two methods, the disclosure concerns the preparation of a compound of formula (IV)

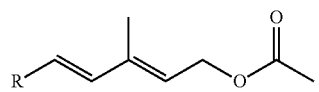
(IV)

in which R is as previously defined for formula (I),
by reacting a compound of formula (V)

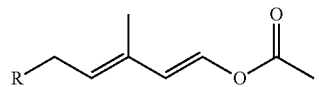
(V)

or by reacting a compound of formula (VI)

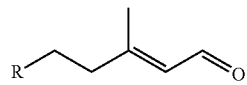
(VI)

via intermediate compound of formula (V). Advantageously, the compound (V) is not isolated.

Thus, any one of the following compounds of formula (I) or (IV): vitamin A acetate, dehydro-β-farnesyl acetate and dehydro-citral acetate can be obtained:

according to the acylation step of the disclosure, from a compound of formula (II) or (V) selected from 11,12-dihydroretinal enol acetate, dehydro-β-farnesyl enol acetate and dehydro-citral enol acetate, respectively, or preferably according to the one-pot acylation/isomerization method according to the disclosure, from a compound of formula (III) or (VI) selected from 11,12-dihydroretinal, farnesal and citral, respectively, without isolating the corresponding acetate intermediate.

The feasibility of the one-pot acylation/isomerization method of the disclosure to obtain vitamin A acetate from 7,8-dihydro-retinal was also observed. According to the disclosure, it can be obtained from dehydro-cyclofarnesyl enol acetate, but preferably in one-pot from cyclofarnesal without isolating the dehydro-cyclofarnesyl enol acetate.

In an advantageous embodiment of the disclosure, the isomerization of compound (II) or (V) into compound (I) or (IV) is carried out in the presence of a strong base, and for example a strong base selected from phosphazenes such as P₂Et, aminides such as 1,8-diazabicyclo[5.4.0]undec-7-ene (DBU) and alcoholates such as potassium tertbutoxide.

The acetylation of compound (III) or (VI) into compound (II) or (V) respectively, is conventionally performed under conditions known to those skilled in the art, for example in the presence of acetic anhydride and pyridine.

Farnesal is an easily accessible reagent. It can indeed be produced synthetically from farnesene, farnesol, ethyl farnesoate, nerolidol or dehydro-nerolidol according to methods known to those skilled in the art (Tetrahedron Letters 2016, 57, 40, 4496-4499; New Journal of Chemistry 2001, 25, 7, 917-929; Catal. Comm. 2014, 44, 40-45), but it can also be isolated from essential oils, such as those of lemongrass. According to an original variant, farnesal can be produced by oxidation of farnesene, under the catalytic conditions of a Wacker-type process in the presence of at least one precious metal, mainly palladium. Advantageously, the reaction medium comprises palladium(II) salts such as $PdCl_2$, copper salts and an oxidizing agent. By way of example, the reaction is carried out in the presence of $PdCl_2$ ($CH_2CH_2$), $CuCl_2$—$LiMoO_4$.

One of the major interests of the disclosure concerned the preparation of a compound of formula (VII)

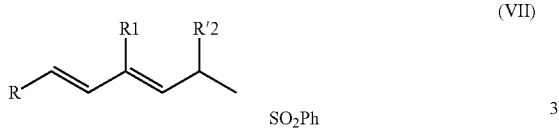

(VII)

in which

R and R1 have the definition which is previously given for formula (I) and R'2 is selected from H and alkyls.

This method is also an advantage of the disclosure, and it includes the steps of:

preparing the sulfone of formula (VII), from a compound of the above-described formula (II), comprising the method of acylating said compound (II) into compound (I), or preparing the sulfone of formula (VII), from a compound of formula (III) comprising the one-pot isomerization/acylation method of said compound into compound of formula (I), said compounds (I), (II) and (III) being as previously defined.

In a variant of the disclosure, dehydro farnesyl sulfone is prepared from farnesal enol acetate.

One of the interests is to produce vitamin A from farnesene or derivatives thereof, and this is another of the advantages of the disclosure, this synthesis comprising at least any one of the methods described above. The different advantages of the disclosure and the applications thereof are illustrated in the following examples.

In the examples, the used abbreviations are defined below:

TT defines the conversion rate;
RR defines a yield on reagent;
$RR_{isolated}$ defines a yield on reagent after isolation;
$RR_{assayed}$ defines a yield on reagent assayed in a reaction medium.

EXAMPLE 1: PREPARATION OF VITAMIN A ACETATE FROM 11,12-DIHYDRORETINAL

This preparation comprises two steps, a first step of obtaining the enol acetate of 11,12-dihydroretinal, which is a subject compound of the disclosure, from the 11,12-dihydroretinal, then a second step of involving the isomerization method of the disclosure of enol acetate of 11,12-dihydroretinal into vitamin A acetate.

1.1) Acetylation of 11,12-Dihydroretinal into Enol Acetate and Isomeric Forms

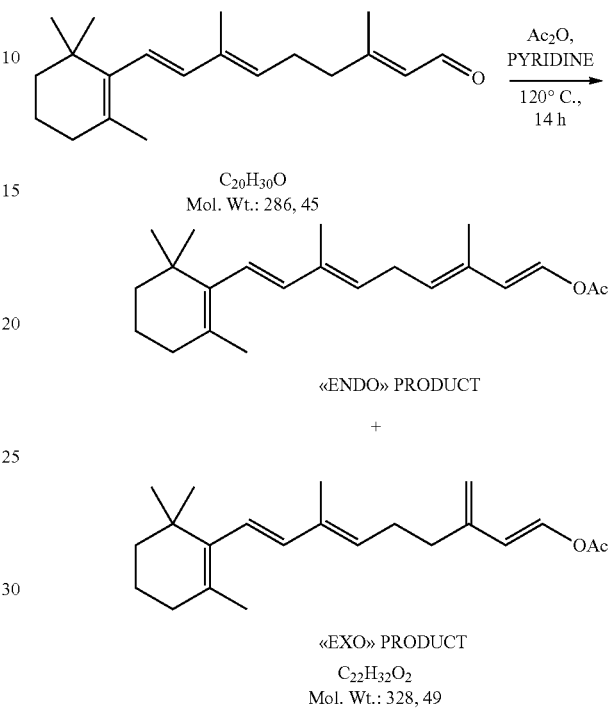

The operating conditions are as follows:
The reagents are introduced under nitrogen in the following order:
11,12-dihydroretinal (DHR), 2 g (4.47 mmol)
DMAP, 1 g (8.10 mmol)
Pyridine, 10 g (126 mmol)
Acetic anhydride, 10 g (96 mmol)

The reaction medium is stirred in the absence of light, at 115° C., for 1 h. After cooling to 25° C., the reaction medium is poured into a mixture consisting of 100 mL of water, 100 mL of saturated aqueous solution of $NaHCO_3$, and 100 mL of cyclohexane. After separation, the aqueous phase is re-extracted with 100 mL of cyclohexane, then the combined organic phases are washed with a saturated aqueous solution of NaCl (300 mL), dried over $Na_2SO_4$ and evaporated.

2.01 g of a yellow-orange colored oil were obtained.
$TT_{DHR}$=100% (TLC)
$RR_{isolated}$=57% of a mixture of exo/endo isomers (80/20)
Titer (HPLC)=41% (33% exo+8% endo).

1.2) Isomerization of Dihydroretinal Enol Acetate into Vitamin a Acetate

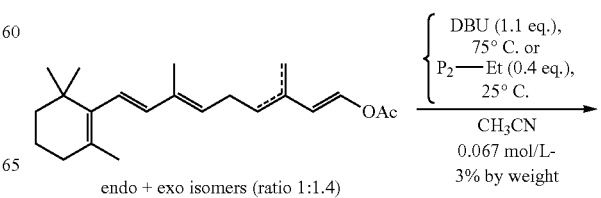

-continued

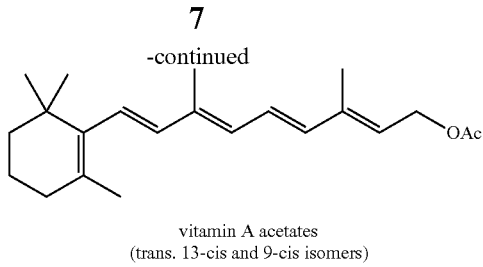

vitamin A acetates
(trans. 13-cis and 9-cis isomers)

The general operating conditions are as follows:

The reagents were introduced under nitrogen into a pillbox provided with magnetic stirring: enol acetates (mixture resulting from the reaction 1.2 above, 50 mg, 0.076 mmol), solvent (1.15 mL, except DMSO: 2.3 mL), base (tBuOK: 3.6 mg (added in solution in the case of DMSO, NMP, isopropanol, and THF); hydrotalcite: 25 mg; KOH: a piece of 30 mg, titer 85%; aqueous soda: 500 µL at 300 g/L). The reaction medium was stirred in the absence of light.

For reaction monitoring, each sample (50 µL) of organic phase is hydrolyzed on a mixture of 0.5 mL of water, 0.5 mL of saturated aqueous solution of $NaHCO_3$, and 0.5 mL of cyclohexane. An aliquot of the cyclohexane phase is deposited on a silica plate and eluted with a cyclohexane/ethyl acetate mixture (90/10).

Different conditions were tested, the most representative are indicated in Table 1.

TABLE 1

| Conditions | assayed RR "trans" (HPLC, %) |
| --- | --- |
| $P_2$-ET (0.2 eq.), 25° C., 30 min | 33 |
| DBU (1.1 eq.), 75° C., 120 min | 59 |
| tBuOK (0.4 eq.), 75° C., 30 min | 19 |

EXAMPLE 2: PREPARATION OF VITAMIN A ACETATE FROM 11,12-DIHYDRORETINAL

This example is the «one-pot» alternative of Example 1 which comprises the acylation/isomerization method according to the disclosure.

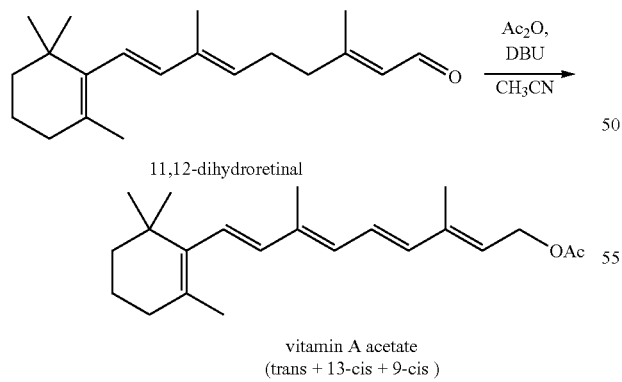

The operating conditions are as follows:
The reagents were introduced under nitrogen in the following order:
Dihydroretinal, 3.62 g (12 mmol)
Acetonitrile, 141.5 g (180 mL)
$Ac_2O$, 1.86 g (18 mmol)
DBU, 9.23 g (60 mmol)

The (homogeneous, dark yellow colored) reaction medium is stirred in the absence of light at 75° C. for 10 h. After cooling to 25° C., the (homogeneous, dark brown colored) reaction medium is poured into a stirred mixture of [cyclohexane (600 mL)+saturated aqueous sodium bicarbonate solution (600 mL)+water (600 mL)]. The aqueous phase (pH=9) is re-extracted with 100 mL of cyclohexane, then the cyclohexane phases are combined, washed with water (100 mL), dried ($Na_2SO_4$), and concentrated to obtain 3.97 g of a red-brown colored oil.

The obtained crude reaction has the following characteristics:
TT (DHR)=100% (TLC),
$RR_{isolated}$=77% of a mixture of (trans+13-cis+9-cis) isomers
Titer (HPLC)=77% (trans+13-cis+9-cis)
Isomeric distribution: trans/13-cis/9-cis=75/16/9.

The above reaction crude was crystallized as follows.
A solution of 3.91 g of the previous oil in 3.8 mL of n-heptane is cooled to −20° C. and seeded with crystals of trans vitamin A acetate (obtained during a previous crystallization in the n-heptane). After 4 h at −20° C., a massive crystallization takes place. The suspension is then cooled to 40° C. for 16 h, then filtered. 2.41 g of orange crystals (after drying) and 4.3 ml (3.37 g) of red-brown mother liquors are obtained.

Characterization of the Crystals:
Crystallization yield of the trans isomer=88%
Trans titer (HPLC)=81%
Titer (trans+13-cis+9-cis, HPLC)=90%
Isomeric distribution: trans/13-cis/9-cis=90/8/2
Characterization of Mother Liquors:
Titer (trans+13-cis+9-cis, HPLC)=23%
Isomeric distribution: trans/13-cis/9-cis=37/37/26

EXAMPLE 3: PREPARATION OF VITAMIN A ACETATE FROM 7,8-DIHYDRORETINAL ACCORDING TO THE «ONE-POT» ALTERNATIVE OF THE DISCLOSURE

This example is another «one-pot» alternative for manufacturing vitamin A acetate which comprises the acylation/isomerization method according to the disclosure.

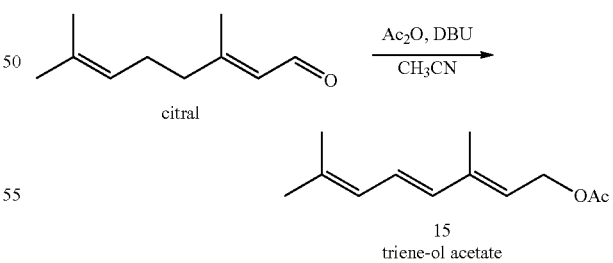

The operating conditions are as follows:
The reagents were introduced under nitrogen at 25° C. in the following order:
7,8-dihydroretinal, 0.2 g (0.628 mmol)
Acetonitrile, 0.42 mL
$Ac_2O$, 0.097 g (0.943 mmol)
DBU, 0.483 g (3.142 mmol)

The (homogeneous, dark yellow colored) reaction medium is stirred in the absence of light, at 80° C. Samples are taken during the reaction for 24 hours.

TT (7,8-DHR)=100% (HPLC)

Assayed $RR_{vitamin\ A\ acetate}$=4% of a mixture of (trans+13-cis+9-cis) isomers after 4 h.

Isomeric distribution: trans/13-cis/9-cis=86/10/4

EXAMPLE 4: PREPARATION OF TRIENE-OL ACETATE FROM CITRAL ACCORDING TO THE «ONE-POT» ALTERNATIVE OF THE DISCLOSURE

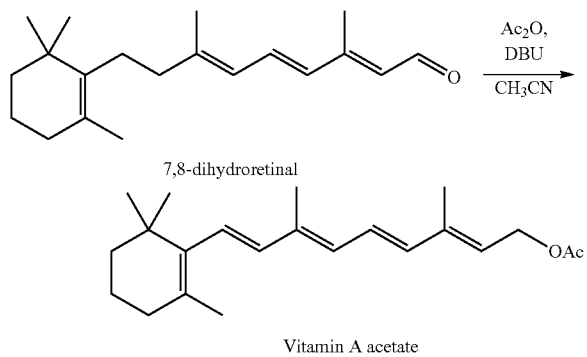

The operating conditions are as follows:

The reagents were introduced under nitrogen in the following order:

Citral, 7.7 g (48 mmol)
Acetonitrile, 72 mL
Ac$_2$O, 7.47 g (72 mmol)
DBU, 36.5 g (240 mmol)

The (homogeneous) reaction medium is stirred in the absence of light at 82° C. for 24 h. After cooling to 25° C., the (homogeneous) reaction medium is poured into a stirred mixture of [cyclohexane (300 mL)+saturated aqueous solution of ammonium chloride (300 mL)+water (300 mL)]. The aqueous phase (pH=5) is re-extracted with 100 mL of cyclohexane, then the cyclohexane phases are combined, dried (Na$_2$SO$_4$), and concentrated to obtain 9.34 g of a brown colored oil.

TT (DHR)=100% (TLC)
$RR_{isolated}$=80%
Titer ($^1$H NMR)=80%

EXAMPLE 5: PREPARATION OF DEHYDROFARNESYL ACETATE FROM FARNESAL ACCORDING TO THE «ONE-POT» ALTERNATIVE OF THE DISCLOSURE

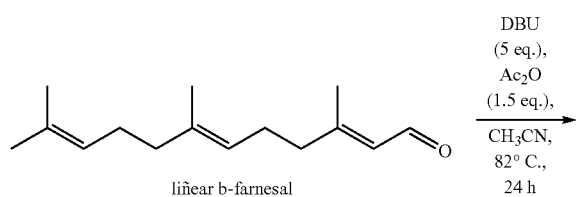

The operating conditions are as follows:

Ac$_2$O is added to a solution of farnesal in CH$_3$CN in a 500 mL three-necked flask equipped with a magnetic stirrer bar and a thermometer, under a nitrogen atmosphere. The medium is stirred at 25° C. for 5 minutes then the DBU is stirred in the reaction medium. The change in the composition of the reaction medium is followed by TLC. After 6 p.m., the conversion of the farnesal is complete. The reaction medium is washed with NH$_4$Cl (2×50 mL), dried over Na$_2$SO$_4$, filtered, then concentrated under reduced pressure (40° C., 10 mbar). The purification by chromatography (SiOH, 120 g, cyclohexane→cyclohexane/AcOEt=98:2) allowed isolating 4.5 g of an orange oil from dehydrofarnesal acetate.

TT Farnesal=100% (GC)
Assayed $RR_{dehydrofarnesal\ acetate}$=89% (GC)
Isolated $RR_{dehydrofarnesal\ acetate}$=75% (chromatography)
Dehydrofarnesal acetate titer=90% ($^1$H NMR estimate)

EXAMPLE 6: PREPARATION OF DEHYDRO-FARNESYlSULFONE FROM DEHYDROFARNESYLACETATE OBTAINED IN EXAMPLE 5

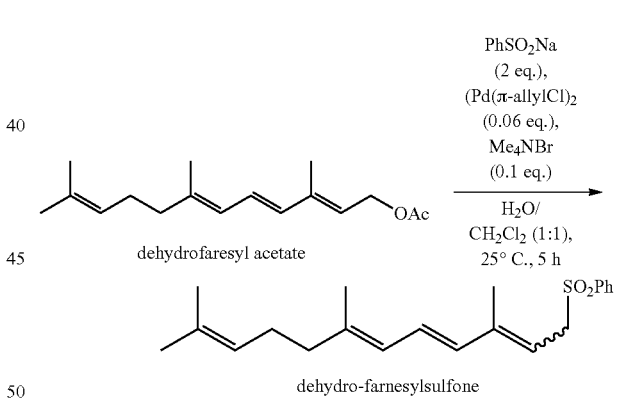

The operating conditions are as follows:

In a Schott tube equipped with a magnetic stirring bar, under a nitrogen atmosphere, is added a solution of Pd(p-allylCl)$_2$ (0.028 g, 0.075 mmoles) and 1,1'-Ferrocenediyl-bis(diphenylphosphine (dppf) (0.126 g, 0.21 mmol) contained in CH$_2$Cl$_2$ (4.4 mL) degassed (N$_2$) is added to a solution of PhSO$_2$Na (1.1 g, 7.57 mmol) and Me$_4$NBr (0.15 g, 0.038 mmol) in H$_2$O (12.4 mL) and dehydrofaresyl acetate (1.1 g, 3.79 mmol) contained in CH$_2$Cl$_2$ (8.8 mL). The evolution of the composition of the reaction medium is followed by TLC of the organic phase. After 5 h at 25° C., the conversion of the dehydrofarnesyl acetate is complete. The reaction medium is extracted with CH$_2$Cl$_2$ (2×20 mL), dried over Na$_2$SO$_4$, filtered, then concentrated under reduced pressure (40° C., 10 mbar). The purification by chromatography (SiOH, 40 g, cyclohexane→cyclohexane/AcoEt=95:5) allowed isolating 1 g of a light yellow oil of dehydro-farnesylsulfone.

TT$_{dehydrofaresyl\ acetate}$=100% (GC)
Assayed RR$_{dehydro-farnesylsulfone}$=76% (GC)
Isolated RR$_{dehydro-farnesylsulfone}$=68% (chromatography)
Dehydro-farnesylsulfone titer=90% ($^1$H NMR estimate)

The invention claimed is:

1. A method for preparing a compound of formula (I)

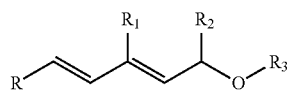
(I)

wherein
R1 is selected from H and alkyls,
R2 is selected from H, alkyls, OR' where R' is selected from alkyls, silyls, CO-alkyl,
R3 is selected from the acyl groups of the CO(R") type, and the CO(OR"), CO(NR"R'"), PO(OR")(OR'"), PO(OR")(R'") groups where R" and R'", independently of each other, are selected from H and alkyls,
R represents a C(R4)=C(R5)(R6) group where R4, R5 and R6, independently of each other, are selected from H, linear or cyclic alkyls and alkenyls, aryls, alkylaryls, or R4 and R5 together form a saturated or unsaturated, substituted or unsubstituted ring,
by reacting a compound of formula (II)

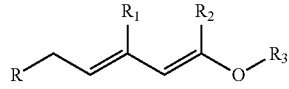
(II)

wherein, R, R1, R2 and R3 have the above definition,
in the presence of a strong base or in the presence of a metal catalyst.

2. A one-pot method for preparing a compound of formula (I)

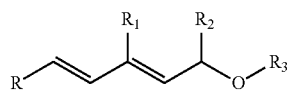
(I)

wherein
R1 is selected from H and alkyls,
R2 is selected from H, alkyls, OR' where R' is selected from alkyls, silyls, CO-alkyl,
R3 is selected from the acyl groups of the CO(R") type, and the CO(OR"), CO(NR"R'"), PO(OR")(OR'"), PO(OR")(R'") groups where R" and R'", independently of each other, are selected from H and alkyls,
R represents a C(R4)=C(R5)(R6) group where R4, R5 and R6, independently of each other, are selected from H, linear or cyclic alkyls and alkenyls, aryls, alkylaryls, or R4 and R5 together form a saturated or unsaturated, substituted or unsubstituted ring,
from a compound of formula (III)

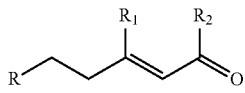
(III)

in which
R, R1 and R2 have the above definition,
said method comprising the following steps:
acylating said compound of formula (III) in a compound of formula (II)

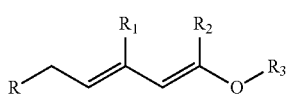
(II)

in which, R, R1, R2 and R3 have the above definition, and
reacting said compound of formula (II), in the presence of a strong base or in the presence of a metal catalyst, to form compound (I).

3. The method according to claim 1, for the preparation of a compound of formula (IV)

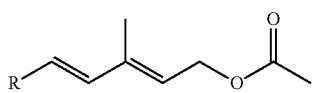
(IV)

wherein R represents a C(R4)=C(R5)(R6) group where R4, R5 and R6, independently of each other, are selected from H, linear or cyclic alkyls and alkenyls, aryls, alkylaryls, or R4 and R5 together form a saturated or unsaturated, substituted or unsubstituted ring,
by reacting a compound of formula (V)

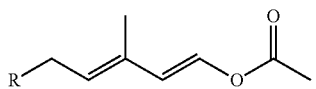
(V)

in the presence of a strong base or in the presence of a metal catalyst,
or
by acylating a compound of formula (VI)

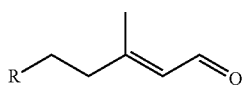
(VI)

in
said compound of formula (V), and
reacting said compound of formula (V) in the presence of a strong base or in the presence of a metal catalyst, to form compound (IV).

4. The method according to claim 1, to obtain a compound of formula (I) selected from vitamin A acetate, dehydro-farnesyl acetate and dehydro-citral acetate, wherein the compound of formula (II) or (V) is selected from 11,12- dihydro-retinal enol acetate, dehydro-farnesyl enol acetate and dehydro-citral enol acetate, respectively.

5. The method according to claim 2, to obtain a compound of formula (I) or (IV) selected from vitamin A acetate, dehydro-farnesyl acetate and dehydro-citral acetate, wherein the compound of formula (III) is selected from 11,12-dihydroretinal or 7,8-dihydroretinal, farnesal and citral, respectively.

6. The method according to claim 1, wherein it is carried out in the presence of a strong base, and for example a strong base selected from phosphazenes, aminides, and alcoholates.

7. The method for preparing a compound of formula (VII)

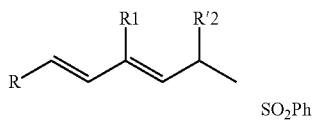

wherein
R1 is selected from H and alkyls,
R'2 is selected from H and alkyls,
R represents a C(R4)=C(R5)(R6) group where R4, R5 and R6, independently of each other, are selected from H, linear or cyclic alkyls and alkenyls, aryls, alkylaryls, or R4 and R5 together form a saturated or unsaturated, substituted or unsubstituted ring,
from a compound of formula (II), comprising the method for acylating said compound (II) into compound (I) according to claim 1, or
from a compound of formula (III) comprising the one-pot isomerization/acylation method of said compound (III) into a compound of formula (I) according to claim 2.

8. The method according to claim 7 for the preparation of dehydro farnesyl sulfone from farnesal enol acetate.

9. A method for synthesizing vitamin A from farnesene, wherein it comprises at least one method according to claim 1.

10. An enol acetate of 11,12-dihydroretinal as an intermediate compound.

11. The method according to claim 3, to obtain a compound of formula (IV) selected from vitamin A acetate, dehydro-farnesyl acetate and dehydro-citral acetate, wherein the compound of formula (V) is selected from 11,12-dihydro-retinal enol acetate, dehydro-farnesyl enol acetate and dehydro-citral enol acetate, respectively.

12. The method according to claim 6, wherein it is carried out in the presence of a strong base, and for example a strong base selected from phosphazenes such as $P_2Et$, aminides such as 1,8-diazabicyclo[5.4.0]undec-7-ene (DBU) and alcoholates such as potassium tertbutoxide.

* * * * *